United States Patent [19]

Mikhail

[11] 4,312,663
[45] Jan. 26, 1982

[54] CYCLICACYLAMINOPERFLUOROALK-ANESULFONANILIDES AND DERIVATIVES THEREOF

[75] Inventor: Ezzat A. Mikhail, New Brighton, Minn.

[73] Assignee: Minnesota Mining and Manufacturing Company, St. Paul, Minn.

[21] Appl. No.: 188,558

[22] Filed: Sep. 18, 1980

[51] Int. Cl.³ .................. A01N 43/08; A01N 41/08; C07C 143/72; C07D 307/68
[52] U.S. Cl. ..................................... 71/88; 71/90; 71/94; 71/95; 71/100; 71/103; 260/239.6; 260/326.47; 260/347.2; 260/397.7 R; 260/455 A; 260/465 D; 544/58.4; 544/159; 544/160; 544/390; 546/225; 548/200; 548/215; 548/343; 549/72; 560/10; 560/13; 564/97

[58] Field of Search ............... 71/88, 100, 103, 90, 71/94, 95; 260/239.6, 397.7 R, 347.2, 465 D, 455 A, 326.47; 560/10, 13; 564/97; 544/58.4, 159, 160, 390; 546/225; 548/200, 215, 343; 549/72

[56] References Cited

U.S. PATENT DOCUMENTS 3,639,474  2/1972  Harrington et al. .................. 564/97
3,894,078  7/1975  Fridinger ....................... 260/501.19
4,005,141  1/1977  Moore et al. ........................ 564/97

*Primary Examiner*—Richard Raymond
*Attorney, Agent, or Firm*—Cruzan Alexander; Donald M. Sell; Lorraine R. Sherman

[57] ABSTRACT

Cyclicacylaminoperfluoroalanesulfonanilides and agriculturally acceptable salts thereof are useful as herbicides and plant growth regulators.

12 Claims, No Drawings

CYCLICACYLAMINOPERFLUOROALKANESULFONANILIDES AND DERIVATIVES THEREOF

TECHNICAL FIELD

This invention relates to cyclicacylaminoperfluoroalkanesulfonanilides and agriculturally acceptable salts thereof which are active as herbicides and plant growth regulators.

BACKGROUND ART

Various N-substituted perfluoroalkanesulfonamide herbicides and plant growth modifiers are known to the art, including, for example, certain acetamido-substituted trifluoromethanesulfonanilides. Thus, see U.S. Pat. Nos. 3,639,474 and 3,894,078.

DISCLOSURE OF INVENTION

The present invention relates to cyclicacylaminoperfluoroalkanesulfonamides of the formula

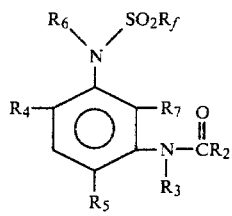

wherein
$R_f$ is lower perfluoroalkyl;
$R_2$ is cycloalkyl; polycycloalkyl; phenyl; nitro-, halo-, alkyl- or alkoxy-substituted phenyl; biphenyl; phenoxy; halophenoxy; phenylalkyl; phenoxyalkyl; halophenoxyalkyl; or a heterocyclic group of 4 to 10 atoms which can contain only carbon, hydrogen, oxygen, sulfur, and nitrogen;
$R_3$ is hydrogen, alkyl, or unsaturated alkyl;
$R_4$ and $R_5$ independently are hydrogen, lower alkyl, cyano, nitro, halo, phenyl, benzoyl, benzenesulfonyl, thio, or phenylthio;
$R_6$ is hydrogen, acyl, alkoxycarbonyl, alkoxythiocarbonyl, haloalkoxycarbonyl, haloalkoxythiocarbonyl, aryloxycarbonyl, or phenylalkoxycarbonyl;
$R_7$ is hydrogen or halogen; and
agriculturally acceptable salts of the acid form compounds (those compounds of the invention in which $R_6$ is hydrogen); provided that
$R_2$, $R_3$, and $R_6$ individually contain not more than twelve carbon atoms.

The term "cyclic" as used herein refers to atoms arranged in a saturated or unsaturated ring structure.

The term "polycycloalkyl" herein means a saturated atomic structure containing two or more rings and up to 14 carbon atoms.

The term "lower" herein means that the indicated group contains not more than four carbon atoms.

Preferably $R_f$ is $CF_3$ in the compounds of the invention. Particularly preferred (due to their relative high herbicidal and plant growth regulator activity) are compounds of formula I in which
$R_f$ is $CF_3$,
$R_2$ is phenyl, phenylalkyl, phenoxyalkyl, cycloalkyl, polycycloalkyl, or a heterocyclic group of 4 to 10 atoms which can contain only carbon, hydrogen, oxygen, sulfur, and nitrogen,
$R_3$ is hydrogen, or alkyl,
$R_4$ and $R_5$ independently are methyl, lower alkyl, or halogen,
$R_6$ is hydrogen, acyl, or ethoxycarbonyl, and
$R_7$ is hydrogen.

The compounds of formula I above, wherein $R_6$ is hydrogen (the acid form compounds), can form salts by replacement of the hydrogen by an agriculturally acceptable cation.

The invention also relates to methods for preparing the compounds, to methods for their use as herbicides, as plant growth regulators, and in herbicidal and plant growth regulating compositions which comprise the compounds dispersed in agriculturally-acceptable extending media.

DETAILED DESCRIPTION

The compounds of the invention (*) are prepared from known precursors as outlined in the following flow chart and the details of their preparation are disclosed in Examples 1–6, below. Preparation of the other compounds on the flow chart are described in the literature and summarized below.

Flow Chart

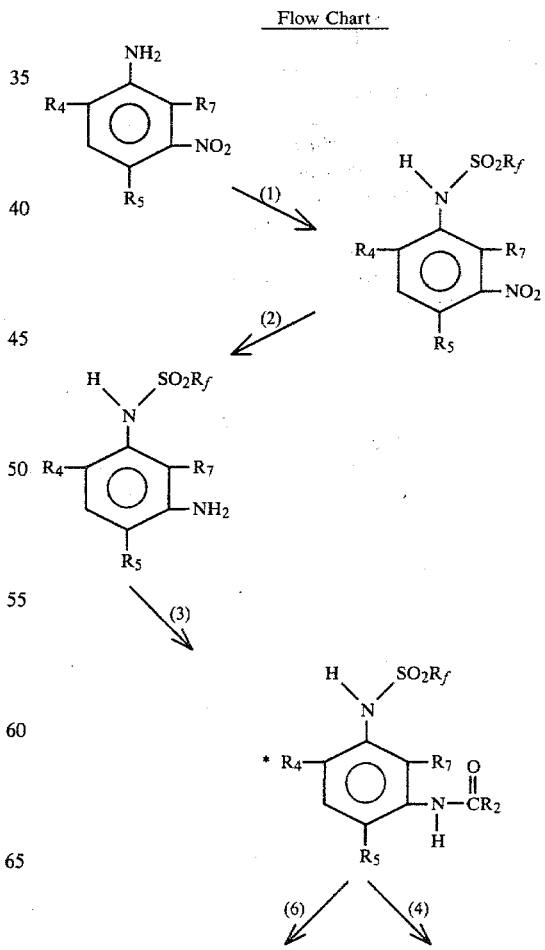

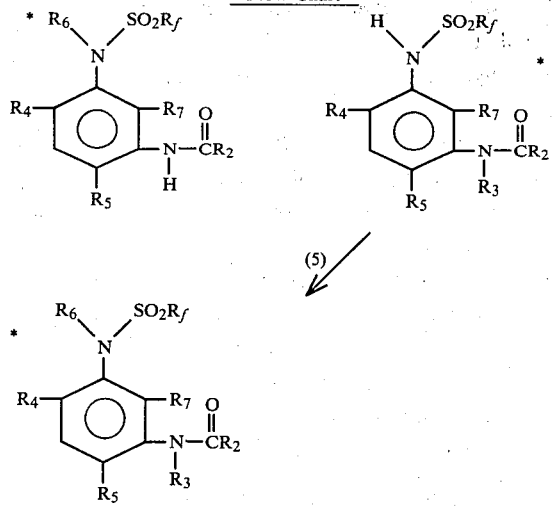

(5)

The starting materials for the process of the invention are nitroaniline and substituted nitroanilines. These compounds are themselves known to the art or may be prepared from known compounds by methods which are well known to the art, for example, by the nitration of a suitably substituted aniline derivative or selective reduction of the desired dinitroaniline derivative.

The reaction of step (1) of the flow chart is carried out utilizing a solution of the appropriate primary arylamine and a suitable acid acceptor (such as triethylamine, dimethylaniline, pyridine and the like) in an inert organic solvent. However, an acid acceptor is not always necessary, and an excess of the primary arylamine may also serve as acid acceptor. Among the suitable solvents are 1,2-dimethoxyethane, benzene, chloroform, dichloromethane, dimethylacetamide, dimethylformamide, and the like. Alternatively an excess of the primary arylamine or the acid acceptor may serve as a solvent, or the reaction may be carried out in the absence of solvent. Generally, a slight excess of an equimolar quantity of the appropriate perfluoroalkane sulfonic anhydride or halide is added to the solution. The addition is advantageously carried out at −15° C. to 50° C., and for some reactants higher or lower temperatures may be preferrable. In cases where the amine is of lower reactivity, it is advantageous to allow the reaction mixture to remain at reflux temperature for a few hours following addition.

The reaction of step (1) may also be carried out in a high pressure reactor. This technique is particularly preferred when perfluoroalkanesulfonyl fluorides are used as reactants. These reactions are usually carried out at temperature ranges of 0° to 150° C., but these temperature ranges may be raised or lowered, depending upon the reactants used. Such reactions are most frequently carried out without solvent, or with dimethylformamide or excess triethylamine as solvent, but other advantageous variations are possible.

It will be appreciated that the scope of this invention encompasses starting materials of a wide range of physical and chemical properties, and the synthetic methods discussed herein are described in general and preferred language. However, a great variation in the use of these synthetic techniques is possible, and this invention is broadly inclusive of such variations.

After completion of the reaction, the product is isolated by conventional methods. For example, the reaction mixture can be extracted with excess aqueous sodium hydroxide. The aqueous extract is then washed with organic solvents and treated with charcoal to remove impurities. Subsequent acidification of the aqueous extract with mineral acid then affords the product as an oil or solid which is distilled, sublimed, chromatographed or recrystallized as required to give pure product. When water soluble solvents are used, the reaction mixture can be poured directly into aqueous mineral acids. The product is then isolated by conventional extraction techniques and purified as above.

Step (2) is a reduction of the nitro group of the intermediate nitroperfluoroalkylsulfonanilide. Chemical or catalytic methods well known to the art are successful. Raney nickel is a suitable catalyst for the reduction and the product is isolated by conventional methods.

Step (3) of the flow chart is carried out by reacting the desired aminoperfluoroalkylsulfonanilide derivative with a slight excess of a compound of the formula $$R_2CQ,$$
$$\parallel$$
$$O$$

wherein Q is halogen, preferably chlorine, or an anhydride residue. The reaction may be carried out in a suitable non-reactive solvents such as amides of organic acids (e.g., N,N-dimethylformamide), ethers (e.g., tetrahydrofuran), chlorinated hydrocarbons (e.g., ethylenedichloride), and the like. It can also be carried out in the absence of solvent. The reaction temperature may be from about 0° C. to 100° C., depending upon the rate of reaction desired. The reaction proceeds readily at room temperature (about 25° C.). The product is isolated by conventional methods.

The reaction of step (4) is carried out by reacting the product of step (3) with one equivalent of $R_3Q$, wherein $R_3$ is as defined for Compound I and Q is halogen, preferably iodine, bromine, or chlorine. The reaction may be carried out in a suitable non-reactive solvent, preferably dimethoxyethane, in the presence of two equivalents of an insoluble acid acceptor such as sodium hydride. The reaction temperature is from about 20° to 80° C., depending upon the rate of reaction desired. After completion of the reaction, the inorganic portion is separated by filtration. The filtrate is concentrated in a vacuum, and the product is purified by recrystallization.

The reaction of step (5) is carried out by reacting the product of step (4) with $R_6Q$, wherein $R_6$ is as defined for Compound I and Q is halogen, preferably iodine, bromine, or chlorine. The reaction may be carried out in a suitable non-reactive solvent, preferably acetone, in the presence of an insoluble acid acceptor such as anhydrous sodium carbonate. The reaction temperature may be from about 20° to 55° C., depending upon the rate of the reaction desired. After completion of the reaction, the inorganic portion is separated by filtration. The filtrate is concentrated in a vacuum, and the product is purified by recrystallization.

The reaction of step (6) is carried out by reacting the product of step (3) with $R_6Q$ using a procedure similar to that of step (5).

The salts of the invention are generally metal, ammonium, and organic amine salts and can be prepared by treating the acid form compound with an appropriate base under mild conditions. Among the metal salts of the invention are alkali metal (e.g., lithium, sodium, and potassium), alkaline earth metal (e.g., barium, calcium, and magnesium) and heavy metal (e.g., zinc and iron) salts as well as other metal salts such as aluminum. Appropriate bases for use in preparing the metal salts include metal oxides, hydroxides, carbonates, bicarbonates, and alkoxides. Some salts are also prepared by cation exchange reactions (by reacting a salt of the invention with an organic or inorganic salt in a cation exchange reaction). The organic amine salts include the salts of aliphatic (e.g. alkyl), aromatic, and heterocyclic amines, as well as those having a mixture of these types of structures. The amines useful in preparing the salts of the invention can be primary, secondary, or tertiary and preferably contain not more than 20 carbon atoms. Such amines include, for example, morpholine, methyl cyclohexylamine, glucosamine, amines derived from fatty acids, etc. The amine and ammonium salts can be prepared by reacting the acid form with the appropriate organic base or ammonium hydroxide. Any of the salts of the types set out above are agriculturally acceptable, the one chosen depending upon the particular use and upon the economics of the situation. Of particular utility are the akali metal, alkaline earth, ammonium, and amine salts.

The salts of the invention are frequently formed by reacting the precursors in aqueous solution. This solution can be evaporated to obtain the salt of the compound, usually as a dry powder. In some cases, it may be more convenient to use a non-aqueous solvent such as alcohols, acetone, etc. The resulting solution is then treated to remove the solvent, for example, by evaporation under reduced pressure.

The herbicidal activity of the compounds of the invention has been determined using screening tests against greenhouse plantings. Both pre- and post-emergence activity were determined in a direct screen against selected weed species. The following are examples of weeds which were used for these tests.

Grasses

Giant Foxtail (*Setaria Faberii*)
Barnyard grass (*Echinochloa crusgalli*)
Crabgrass (*Digitaria ischaemum*)
Quackgrass (*Agopyron repens*)
Yellow Nutsedge (*Cyperus esculentus*)

Broadleaves

Pigweed (*Amaranthus retroflexus*)
Purslane (*Portulaca oleracea*)
Wild Mustard (*Brassica kaber*)
Wild Morning Glory (*Convolvulus arvensis*)

The test chemicals were dissolved in a small amount of acetone or other suitable solvent and then diluted with water to give a concentration of 2000 ppm. From this concentration aliquots were diluted to give a final concentration of 500 ppm. Eighty ml. of this solution were added to a 6-inch pot containing the weed seeds to give a concentration equivalent of 20 lb/acre. Use of 20 ml. of said solution gives a concentration equal to 5 lb/acre. All subsequent waterings were made from the bottom. Two pots were used per treatment. Data were taken 2 to 3 weeks after treatment and recorded as percent pre-emergence kill for each species compared to the untreated controls.

To assess post-emergence activity, the same weed mixtures were allowed to grow from two to three weeks until the grasses were approximately 1 to 3 inches and the broadleaves 1 to 1½ inches tall. They were sprayed for approximately 10 seconds or until good wetting of the leaf surfaces occurred with a 2000 ppm solution as described above. Data were taken two to three weeks after treatment and recorded as percent kill for each species compared to the untreated controls.

The compounds of this invention are broadly active as herbicides and show various types of plant growth modifying activity. Plant growth modification as defined herein consists of all deviations from natural development, for example, defoliation, stimulation, stunting, retardation, desiccation, tillering, dwarfing, regulation, and the like. This plant growth modifying activity is generally observed as the compounds of the invention begin to interfere with certain processes within the plant. If these processes are essential, the plant will die if treated with a sufficient dose of the compound. However, the type of growth modifying activity observed varies among types of plants.

The compounds of the invention have been found to be particularly effective in controlling established rhizomatous Johnsongrass (*Sorghum halepense*, L. Pers.). The control of rhizomatous Johnsongrass is especially important since it is not ordinarily controlled effectively at an application rate that is tolerant to crops by commercially available herbicides (although seedling Johnsongrass is susceptible to several commercial herbicides).

For application to plants, the compounds can be finely divided and suspended in any of the usual aqueous media. In addition, spreading agents, wetting agents, sticking agents, or other adjuvants can be added as desired. Dry powders, as such, or diluted with inert materials such as diatomaceous earth, can likewise be used as dusts for this purpose. The preparations are coated on the plants or the ground is covered with them when preemergence control is desired. Application is made with the usual sprayers, dust guns and the like. Application rates are at 0.5 to 20 lbs/acre in general, but may be increased or reduced according to individual circumstances of use.

Since certain compounds of the invention are particularly active against Johnsongrass, it is advantageous to combine them with other known herbicides to broaden or maximize the weed spectrum controlled by herbicidal compositions of this invention or to better control a weed not well controlled by specific compounds of the invention. Furthermore, herbicidal composition containing compounds of the invention may contain, in addition, nematicides, fungicides, insecticides, fertilizers, trace metals, soil conditioners, other plant growth regulators, and the like. Such combinations are clearly envisioned in this invention.

The following examples are given for the purpose of further illustrating the present invention but are not intended, in any way, to be limiting of the scope thereof. All parts are given by weight unless otherwise specifically noted. The individual infrared spectra coincide with the assigned structures.

EXAMPLE 1

Preparation of 2,4-dimethyl-5-nitrotrifluoromethanesulfonanilide according to step (1)

This compound was prepared from 2,4-dimethyl-5-nitroaniline by use of a substantially equimolar quantity of trifluoromethanesulfonylfluoride, an acid acceptor such as triethylamine, and an inert organic solvent such as chloroform, m.p. 80°–82° C.

|  | Found | Calculated |
|---|---|---|
| Elementary analysis: | C 36.3 | C 36.2 |
|  | H 3.1 | H 3.0 |
|  | N 9.4 | N 9.4 |

EXAMPLE 2

Preparation of 5-amino-2,4-dimethyltrifluoromethanesulfonanilide according to step (2)

2,4-Dimethyl-5-nitrotrifluoromethanesulfonanilide (29.8 g, 100 mmole) was dissolved in ethanol (400 ml) and then reduced over Raney nickel at about 45 psi of hydrogen gas. After the hydrogen uptake was complete, the catalyst was deactivated with elementary sulfur, the reaction mixture was filtered, and the filtrate was evaporated under reduced pressure to give the product as a white solid, m.p. 149°–150° C.

|  | Found | Calculated |
|---|---|---|
| Elementary analysis: | C 40.2 | C 40.3 |
|  | H 4.1 | H 4.1 |
|  | N 10.4 | N 10.4 |

EXAMPLE 3

Preparation of 2-chloro-5-(cyclopropanecarbonyl)amino-4-methyltrifluoromethanesulfonanilide according to step (3)

To 5-amino-2-chloro-4-methyltrifluoromethanesulfonanilide (2.88 g, 10 mmoles) in toluene (15 ml), cyclopropanecarboxylic acid chloride (1.25 g, 12 mmoles) was added slowly dropwise. The reaction mixture was maintained at its refluxing temperature for 10 hours, then cooled to 10° C. for 2 hours. The product, filtered and recrystallized, had a melting point of 198°–200° C.

|  | Found | Calculated |
|---|---|---|
| Elementary analysis: | C 40.1 | C 40.4 |
|  | H 3.3 | H 3.2 |
|  | N 7.9 | N 8.0 |

The following compounds were prepared utilizing the same general method:
5-(2'-chlorobenzoyl)amino-2-chloro-4-methyltrifluoromethanesulfonanilide, m.p. 178°–180° C.
5-(2'-chlorobenzoyl)amino-2,4-dimethyltrifluoromethanesulfonanilide, m.p. 175°–176° C.
5-(2'-bromobenzoyl)amino-2,4-dimethyltrifluoromethanesulfonanilide, m.p. 180°–181° C.

EXAMPLE 4

Preparation of 5-benzoylamino-2,4-dimethyltrifluoromethanesulfonanilide according to step (3)

5-Amino-2,4-dimethyltrifluoromethanesulfonanilide (10.72 g., 40 mmoles) was dissolved in chloroform (100 ml.) and triethylamine (8.08 g., 80 mmoles) was added. The solution was cooled to a temperature of 0° to 5° C. To this solution benzoyl chloride (5.62 g., 40 mmoles) was added slowly dropwise. The reaction mixture was then heated to its reflux temperature for 12 hours. The mixture was evaporated to dryness under vacuum. The solid was added to water (100 ml.), and the aqueous suspension was acidified with dilute hydrochloric acid at 0° to 5° C. The product was collected, washed thoroughly with water, and dried at 60° C. under vacuum, m.p. 219.5°–222° C.

|  | Found | Calculated |
|---|---|---|
| Elementary Analysis: | C 52.0 | C 51.6 |
|  | H 4.2 | H 4.0 |
|  | N 7.5 | N 7.5 |

The following compounds were also prepared utilizing the same general method, but substituting the appropriate precursors:

2,4-dimethyl-5-(4'-methoxybenzoyl)aminotrifluoromethanesulfonanilide, m.p. 202°–203° C.
5-(2',4'-dichlorobenzoyl)amino-2,4-dimethyltrifluoromethanesulfonanilide, m.p. 174°–179° C.
5-(cyclopropanecarbonyl)amino-2,4-dimethylcarboxamidotrifluoromethanesulfonanilide, m.p. 201°–203° C.
5-(4'-biphenylcarbonyl)amino-2,4-dimethyltrifluoromethanesulfonanilide, m.p. 208°–210° C.
5-(4'-biphenylcarbonyl)amino-2-chloro-4-methyltrifluoromethanesulfonanilide, m.p. 207°–209° C.
5-benzylcarboxamido-2,4-dimethyltrifluoromethanesulfonanilide, m.p. 145°–149° C.
5-(benzylcarbonyl)amino-2-chloro-4-methyltrifluoromethanesulfonanilide, m.p. 151°–153° C.
5-benzoylamino-2-chloro-4-methyltrifluoromethanesulfonanilide, m.p. 200°–202° C.
2-chloro-4-methyl-5-(phenoxyacetyl)aminotrifluoromethanesulfonanilide, m.p. 202°–205° C.
2,4-dimethyl-5-(phenoxyacetyl)aminotrifluoromethanesulfonanilide, m.p. 182°–186° C.
2,4-dimethyl-5-(2'-furancarbonyl)aminotrifluoromethanesulfonanilide, m.p. 195°–196° C.
5-(1'-adamantanecarbonyl)amino-2,4-dimethyltrifluoromethanesulfonanilide, m.p. 218°–220° C.
2-chloro-5-(2'-furancarbonyl)amino-4-methyltrifluoromethanesulfonanilide, m.p. 183°–184° C.

EXAMPLE 5

Preparation of 2,4-dimethyl-5-(N-ethyl-N-cyclopropanecarbonyl)aminotrifluoromethanesulfonanilide according to step (4)

5-(Cyclopropanecarbonyl)amino-2,4-dimethyltrifluoromethanesulfonanilide (8.8 g, 25 mmoles) was added portionwise to a stirred suspension of sodium hydride (2.64 g of 50% oil dispersion, 55 mmoles) in glyme (100 ml) under a nitrogen atmosphere. The reaction mixture was then heated to its reflux temperature for 2 hours. The reaction mixture was cooled to a temperature of 15° C. To this suspension ethyl iodide (3.9 g, 25 mmoles) was added slowly and the reaction mixture was again heated to its reflux temperature for 2 hours. The mixture was evaporated to dryness under vacuum, and water (100 ml) was then added to the residue. The aqueous solution was washed twice with methylene chloride (50 ml) for purification purposes. The aqueous solution was acidified and the product extracted with methylene chloride. The organic extract was washed with water (25 ml) and dried over magnesium sulfate and filtered. The organic extract was evaporated to dryness under vacuum. The product was crystallized from hexane and chloroform, m.p. 182°–184° C.

|  | Found | Calculated |
|---|---|---|
| Elementary analysis: | C 49.8 | C 49.5 |
|  | H 5.4 | H 5.2 |
|  | N 7.7 | N 7.7 |

EXAMPLE 6

Preparation of 2,4-dimethyl-5-(N-ethyl-N-cyclopropanecarbonyl-)amino-$N_1$-ethoxycarbonyltrifluoromethanesulfonanilide according to step (5)

2,4-Dimethyl-5-(N-ethyl-N-cyclopropanecarbonyl-)aminotrifluoromethanesulfonanilide (1.9 g 5.2 mmoles) was dissolved in acetone (20 ml). To this solution anhydrous sodium carbonate (1.06 g, 10 mmoles) was added. Ethyl chloroformate (1.09 g 10 mmoles) was then added dropwise. The reaction mixture was stirred at room temperature for about 10 hours, then filtered through a filter cell and the solvent was evaporated under vacuum. The product was purified by column chromatography using a solution of 15% acetone/dichloromethane as eluent. The product was obtained as a viscous oil.

|  | Found | Calculated |
|---|---|---|
| Elementary analysis: | C 49.1 | C 49.5 |
|  | H 5.1 | H 5.3 |
|  | N 6.1 | N 6.4 |

EXAMPLE 7

Preparation of 5-benzamido-$N_1$-ethoxycarbonyl-2,4-dimethyltrifluoromethanesulfonanilide according to step (6)

5-(Benzoyl)amino-2,4-dimethyltrifluoromethanesulfonanilide (3.72 g, 10 mmoles) was dissolved in acetone (25 ml). To this solution anhydrous sodium carbonate (2.12 g, 20 mmoles) was added. Ethyl chloroformate (2.18 g, 20 mmoles) was then added dropwise. The reaction mixture was stirred at room temperature for about 12 hours and was then filtered through a filter cell and the solvent was evaporated under vacuum. The product was recrystallized from hexane and chloroform, m.p. 154°–156° C.

|  | Found | Calculated |
|---|---|---|
| Elementary analysis: | C 51.4 | C 51.2 |
|  | H 4.3 | H 4.2 |
|  | N 6.3 | N 6.4 |

The following compound was prepared utilizing the same general method:

5-(cyclopropanecarbonyl)amino-$N_1$-cyclopropanecarbonyl-2,4-dimethyltrifluoromethanesulfonanilide, m.p. 153°–155° C.

What is claimed is:

1. A compound of the formula

[Structure: benzene ring with substituents $R_6$ and $SO_2R_f$ on N at top, $R_4$ at left, $R_7$ and $N(R_3)$-$\overset{O}{\underset{\|}{C}}R_2$ at right, $R_5$ at bottom]

wherein $R_f$ is lower perfluoroalkyl;

$R_2$ is cycloalkyl; polycycloalkyl; phenyl; nitro-, halo-, alkyl- or alkoxy- substituted phenyl; biphenyl; phenylalkyl; phenoxyalkyl; halophenoxyalkyl; or a heterocyclic group of 4 to 10 atoms, which can contain only carbon, hydrogen, oxygen, sulfur, and nitrogen;

$R_3$ is hydrogen, alkyl, or unsaturated alkyl;

$R_4$ and $R_5$ are independently hydrogen, lower alkyl, cyano, nitro, halo, phenyl, benzoyl, benzenesulfonyl, or phenylthio;

$R_6$ is hydrogen, acyl, alkoxycarbonyl, alkoxythiocarbonyl, haloalkoxycarbonyl, haloalkoxythiocarbonyl, aryloxycarbonyl, or phenylalkoxycarbonyl, and agriculturally acceptable salts of the acid form compounds;

$R_7$ is hydrogen or halogen;

provided that $R_2$, $R_3$, and $R_6$ individually contain not more than twelve carbon atoms.

2. A compound of the formula

[Structure: benzene ring with substituents $R_6$ and $SO_2CF_3$ on N at top, $R_4$ at left, $N(R_3)$-$\overset{O}{\underset{\|}{C}}R_2$ at right, $R_5$ at bottom]

wherein $R_2$ is cycloalkyl; polycycloalkyl; phenyl; halo- or alkoxy-substituted phenyl; biphenyl; phenylalkyl; phenoxyalkyl; or a heterocyclic group of 4 to 10 atoms, which can contain only carbon, hydrogen, oxygen, sulfur, and nitrogen;

$R_3$ is hydrogen or lower alkyl;

$R_4$ is halo or lower alkyl;

$R_5$ is lower alkyl; and $R_6$ is hydrogen or alkoxycarbonyl, and agriculturally acceptable salts of the acid form compounds;

provided that $R_2$ and $R_6$ individually contain not more than twelve carbon atoms.

3. A compound of the formula

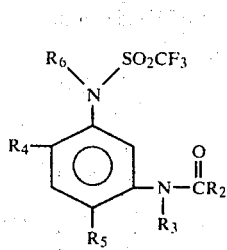

wherein

R₂ is cyclopropyl, adamantyl, phenyl, halo-substituted phenyl, methoxy-substituted phenyl, biphenyl, benzyl, phenoxymethylene, or furyl;

R₃ is hydrogen or ethyl;

R₄ is halo or methyl;

R₅ is methyl;

R₆ is hydrogen or ethoxycarbonyl, and agriculturally acceptable salts of the acid form compounds.

4. A compound 5-(cyclopropanecarbonyl)amino-2,4-dimethyltrifluoromethanesulfonanilide.

5. A compound 5-(cyclopropanecarbonyl)amino-N₁-cyclopropylcarbonyl-2,4-dimethyltrifluoromethane sulfonanilide.

6. A compound 2-chloro-5-(cyclopropanecarbonyl)amino-4-methyltrifluoromethanesulfonanilide.

7. A compound 2,4-dimethyl-5-(2'-furancarbonyl)aminotrifluoromethanesulfonanilide.

8. A compound 2-chloro-5-(2'-furancarbonyl)amino-4-methyltrifluoromethanesulfonanilide.

9. A compound 5-(1'-adamantanecarbonyl)amino-2,4-dimethyltrifluoromethanesulfonanilide.

10. A compound 2,4-dimethyl-5-(4'-methoxybenzoyl)aminotrifluoromethanesulfonanilide.

11. A method for terminating the life cycle of higher plants which comprises contacting said plants with an effective amount of a compound according to claim 1.

12. A herbicidal composition which consists essentially of a compound according to claim 1 dispersed in an agriculturally acceptable extending medium.

* * * * *